United States Patent [19]

Ushio et al.

[11] Patent Number: 5,185,372
[45] Date of Patent: Feb. 9, 1993

[54] STABLE AQUEOUS PREPARATION

[75] Inventors: Kazumichi Ushio, Nishinomiya; Kenichi Yoshida, Itami, both of Japan

[73] Assignee: Senju Pharmaceutical Company, Limited, Osaka, Japan

[21] Appl. No.: 751,885

[22] Filed: Aug. 29, 1991

[30] Foreign Application Priority Data

Aug. 30, 1990 [JP] Japan .................................. 2-229888

[51] Int. Cl.$^5$ ............................................. A61K 31/07
[52] U.S. Cl. .................................. 514/552; 514/912; 514/725
[58] Field of Search ..................... 514/725, 912, 552

[56] References Cited

U.S. PATENT DOCUMENTS 5,032,392 7/1991 Varma .................................. 514/725

OTHER PUBLICATIONS

Remington's Pharmaceutical Sciences, Fifteenth Edition. 1975. p. 1467.
Physician's Desk Reference for Ophthamology, 16 Edition, 1988. pp. 204, 87.

Primary Examiner—Frederick E. Waddell
Assistant Examiner—Zohreh A. Fay
Attorney, Agent, or Firm—Millen, White, Zelano and Branigan

[57] ABSTRACT

Presented is a stable aqueous preparation for ophthalmic topical administration containing vitamin A or a vitamin A derivative having vitamin A activities to be used for the treatment of dry eye syndrome characterized in that it contains a buffering component selected from the group consisting of phosphoric acid, boric acid, citric acid, glutamic acid, ε-aminocaproic acid and the alkali metal salts thereof, a non-ionic surfactant and a chelating agent, that its acidity is adjusted in the range of pH 5 to pH 8, and that it is filled in a tight container made of polypropylene or polyethylene terephthalate.

2 Claims, No Drawings

STABLE AQUEOUS PREPARATION

BACKGROUND OF THE INVENTION

The present invention relates to an aqueous preparation containing vitamin A or its derivative which may be used for the treatment of dry eye syndrome represented by lacrimal hyposecretion, squamous metaplasia and the like. More specifically the present invention relates to an aqueous preparation containing vitamin A or its derivative and having a stability which allows the use of the preparation as an ophthalmic pharmaceutical preparation.

The cornea is an avascular tissue forming the front surface of the eyeball, and it has transparency and a constant curvature which are necessary to correctly introduce light from the environment into the eyeball. To maintain transparency of the cornea, it is the fundamental requirement that each of the 5 layers constituting the cornea, i.e. the corneal epithelium, the Bowman's membrane, the corneal stroma, the Descemet's membrane and the corneal endothelium, is regularly arranged and performs its normal physiological functions. Since the cornea is an avascular tissue, its supplies of nutrients required for the maintenance of its functions are dependent on the perilimbal capillary loops, the aqueous humor and the tear fluid, and the corneal epithelium, in particular, is exclusively dependent on the tear fluid for the nutrient supplies. In addition, the corneal epithelium is protected by the tear film from the air and the mechanical stimulation which may be caused by friction with the palpebral conjunctiva.

Since the corneal epithelium is constantly exposed to the air, except when the eyelids are closed, the water in the tear fluid which covers the cornea is constantly lost by evaporation, and the loss is supplemented by a continuous production of the tear fluid. The production of the tear fluid is made cooperatedly by the lacrimal gland, the goblet cells and the meibomian glands. Their functions may be lowered by a variety of extraocular disorders and systemic disorders such as autoimmune diseases as well as aging. When the function to produce the tear fluid is lowered, the corneal epithelium tends to become dried, the physiological state of the corneal epithelium is thus disturbed, and the occurrence of inflammation is promoted, which may lead to corneal injury, corneal opacification or vascular infiltration into the cornea. Moreover, it is known that since the cornea is an extremely sensitive site, only a very slight tendency to dryness may cause an uncomfortable sensation such as photophobia, pain, a feeling of the presence of a foreign body and the like, thus hindering daily life, and may cause severe symptoms in some cases.

Vitamin A and its derivatives are known to be effective on such pathological states [e.g. J. L. Ubels et al., Current Eye Research, 10 (4), 1049 (1985)], and based on these reports, topical preparations which contain an effective amount of vitamin A or a derivative thereof having vitamin A activities (in the description hereinafter, the simple wording "vitamin A" refers to "vitamin A and its derivatives having vitamin A activities ", unless derivatives of vitamin A are clearly excluded according to the context) have come to be applied. Among, others, preparations in the form of aqueous eye drops have been needed so as to allow appropriate administration by patients themselves, since it is necessary to repeatedly administer vitamin A over a period of time in order to treat patients with a variety of uncomfortable symptoms and severe damages caused by the tendency to dryness of the cornea and conjunctiva.

However, vitamin A and its derivatives are extremely unstable compounds. It is known that, inter alia, in aqueous preparations, their loss is likely to be elevated to an extreme degree due to the adsorption to the container as well as decomposition, thus resulting in a rapid degrading of product quality during storage. Consequently, it is extremely difficult to produce an aqueous preparation stably containing an effective amount of vitamin A. Thus, a vitamin A aqueous preparation which is satisfactory has not been put into practical use.

The inventors made an extensive study to solve the problem. Finally, the inventors have succeeded in solving the thus-far insurmountable problem and produced a stable aqueous preparation which can be used as an eye drop by incorporating, during production of a vitamin A preparation, a buffering component selected from the group consisting of phosphoric acid, boric acid, citric acid, glutamic acid, $\epsilon$-aminocaproic acid and the alkali metal salts thereof, a non-ionic surfactant and a chelating agent, and adjusting the acidity in the range of pH 5 to pH 8, and filling into an air-tight container made of polypropylene or polyethylene terephthalate.

SUMMARY OF THE INVENTION

The present invention, therefore, is an aqueous preparation containing a vitamin A derivative which may be used for the treatment of dry eye syndrome characterized in that it is a stable aqueous preparation containing a buffering component selected from the group consisting of phosphoric acid, boric acid, citric acid, glutamic acid, $\epsilon$-aminocaproic acid and the alkali metal salts thereof, a non-ionic surfactant and a chelating agent, having the acidity adjusted in the range of pH 5 to pH 8, and filled in an air-tight container made of polypropylene or polyethylene terephthalate.

DETAILED DISCUSSION

The main active constituent of the aqueous preparation of the present invention is vitamin A (retinol) or a vitamin A derivative having vitamin A activities. The vitamin A derivatives having vitamin A activity include, for example, esters of vitamin A such as retinol palmitate and retinol acetate, and any vitamin A derivative having vitamin A activities may conveniently used as the active constituent of the aqueous preparation of the present invention.

The concentration of vitamin A in the aqueous preparation of the present invention may be properly determined in accordance with the purpose of use of the preparation. In the case where it is used as an eye drop for the treatment of dry eye syndrome, vitamin A or its derivative having vitamin A activities as mentioned above may usually be incorporated at a concentration in the range of 50 I.U./ml to 20,000 I.U./ml, preferably 500 to 3000 I.U./ml, most preferably 1000 to 2000 I.U./ml ("I.U." indicates the vitamin A international unit, which is followed hereinafter).

The present inventors carried out an intensive study to create an aqueous preparation containing vitamin A and having the stability which allows the preparation to be used commercially as a pharmaceutical preparation.

As a result, it was found that an aqueous preparation which is stable enough in the acidity range adapted to be used as an eye drop, i.e. pH 5 to pH 8, may be obtained by emulsifying vitamin A in water in the presence of a non-ionic surfactant and then adding a buffering agent selected from the group consisting of phosphoric acid, boric acid, citric acid, glutamic acid, ε-aminocaproic acid and the alkali metal salts thereof. An additional extensive study made it clear that the stability of the preparation can be further improved by the addition of a chelating agent. However, the aqueous preparation of vitamin A thus obtained was not sufficiently improved concerning the adsorption of vitamin A into the container, which was commonly observed in vitamin A preparations. Thus, a further improvement in compatibility with the container was needed. The present inventors carried out a further study for a container which may not adsorb vitamin A contained in the preparation obtained above, and found out that the adsorption of vitamin A to the container was substantially prevented only when a container made of polypropylene or polyethylene terephthalate was utilized. On the other hand, it was known that vitamin A is readily oxidized by oxygen in the air. Thus, it was found that the vitamin A contained underwent oxidation during storage and that the rapid lowering of its content during storage could not be prevented. Therefore, a study was made in search of a method which may allow a long-term storage of the aqueous preparation. As a result, a preparation which may stand a long-term storage was successfully obtained by enclosing, with an oxygen scavenger, the above preparation, which was filled in a container made of polypropylene or polyethylene terephthalate, in another container substantially impermeable to oxygen.

In the aqueous preparation of the present invention, a non-ionic surfactant is used in order to form an emulsion by dispersing vitamin A in the aqueous medium. For a non-ionic surfactant, any of the non-ionic surfactants which are conventionally used as constituents of eye drops may be conveniently used. For example, either of polysorbate 80 and polyoxyethylenehydrogenated castor oil may advantageously be used. The ratio of the content of the non-ionic surfactant to that of vitamin A in the preparation may be suitably selected according to the purpose of use and the way of administration, although it necessarily has to be large enough to form a stable emulsion of vitamin A in the aqueous preparation. When used as an eye drop for the treatment of the dry eyes, the non-ionic surfactant is preferably added in the equivalent or more amount to that of vitamin A. Particularly preferably, the non-ionic surfactant may be used in the range of 1.5 to 5 parts by weight, preferably 2 to 4 parts by weight in respect to 1 part by weight of vitamin A.

In the aqueous preparation of the present invention is added a buffering agent selected from the group consisting of boric acid, citric acid, glutamic acid, ε-aminocaproic acid and their alkali metal salts. For alkali metal salts, sodium salts and potassium salts may be conveniently used. When necessary, the buffering agents may be used in combination of two or more of them.

A chelating agent may be added in the aqueous preparation of the present invention. For a chelating agent, any of the chelating agents which are conventionally used as constituents of eye drops may be conveniently used. For example, sodium edetate and sodium citrate may be advantageously used. The amount of the chelating agent to be used may usually be in a range of about 0.001% to about 0.1% of the total amount of the aqeous preparation. It has been found that the addition of a chelating agent not only sharply improves the stability of the aqueous preparation of the present invention but also increases the effect of the preservative, as will be mentioned later.

In the aqueous preparation of the present invention, a preservative may be added as in the cases of usual aqueous preparations so as to prevent any growth of microorganisms after opening the container. For preservatives to be added, the preservatives of the type of quaternary ammonium salts such as benzalkonium chloride and of the type of chlorhexidines such as chlorhexidine digluconate may advantageously used. Other preservatives also may naturally be used insofar as they meet the object of the present invention. It is known that the effect of the preservatives is often reduced in aqueous preparations containing non-ionic surfactants. However, it has been found that if boric acid or its alkali metal salt is used the reduction of the effect of the preservatives may be prevented even when a non-ionic surfactant is contained in relatively a high amount, as mentioned already. Therefore, the use of boric acid or its alkali metal salts enables to reduce the quantity of preservatives (which might cause a local irritation). In this case, the amount of boric acid or borax (sodium borate) is preferably in the range of 0.5% to 2.5%, particularly in the range of 1.0% to 2.0%.

It is known that vitamin A, the main constituent of the aqueous preparation of the present invention, may be adsorbed to various containers. For example, it is known that when stored in a container made of polyethylene, vitamin A in the preparation being markedly adsorbed, the concentration of vitamin A in the preparation lowers rapidly. The present inventors made a screening for a container that can minimize the adsorption of vitamin A, and found that adsorption to the container comes to be negligible when a polypropylene or a polyethylene terephthalate container is used. Any of such containers adapted to the use as containers for liquid preparation may usually be utilized conveniently.

As vitamin A is quite susceptible to oxidation as mentioned above, it is still difficult to avoid the influence of oxygen in the air even when a polypropylene or polyethylene terephthalate container is used. Then, investigations were made in search of a countermeasure to this. As a result, it was found that the influence of oxygen can be minimized by enclosing, with an oxygen scavenger, the aqueous preparation, filled in a container mentioned above, in another container which substantially impermeable to oxygen so as to minimize the effect of oxygen. For a such container substantially impermeable to oxygen, a bag-shaped or tubular container made of a film composed of a oxygen-impermeable polymer membrane laminated with an aluminum foil may preferably used, although any of sealable containers made of a material substantially impermeable to oxygen may conveniently used. For example, containers made of polyethylene, polypropylene, polyvinylalcohol, polyvinylydene chloride and the like may also be used likewise.

Besides, unless it opposes the object of the present invention, the aqueous preparation of the present invention may also contain other pharmacologically active ingredients than vitamin A such as vitamin E, and it may also contain isotonizers such as sodium chloride and glycerol and the like when they are required according to the purpose of use. Thus, the inventors have succeeded in the development of an aqueous preparation containing vitamin A as a main ingredient, the preparation thus far considered hardly possible to develop for practical use due to the adsorption to the container and rapid degradation in aqueous preparations.

Effect of the Invention

The test results concerning the aqueous preparation containing vitamin A as a main constituent, which is provided by the present invention, will be described below to show the effect of the present invention.

1. pH And Stability Of The Aqueous Preparation

Vitamin A palmitate was emulsified with a borate buffer system and stored for 1 week at 50° C. and 40° C. to examine the change in vitamin A content in the aqueous preparation. The following results were obtained.

When stored at 50° C., the remaining rate in the samples of pH 4.0 and pH 8.0 was 83.9% and 86.4%, respectively, whereas the remaining rate was more than 90% in any of the samples which had a pH value between 5.0 and 7.5. On the other hand, when stored at 40° C., the remaining rate in the samples having a pH value between 5.0 and 7.0 was 95 to 96%, indicating a notable stability in comparison with the remaining rate in the samples of pH 4.0 and pH 9.0, i.e. about 90%. The appearance of the emulsion of these samples remained unchanged.

2. Effect Of Buffer System On Stability

For evaluation of buffer systems, the aqueous preparations of pH 5.8 were prepared using different buffer systems based on sodium acetate, borax, citric acid, ε-aminocaproic acid, sodium glutamate, sodium hydrogen phosphate and taurine. They were stored for 2 weeks at 40° C. under protection from light with aluminum foil, and measured for the remaining rate. The following results were obtained.

The remaining rate was 81 to 84% in sodium acetate buffer system and taurine buffer system, and about 88% in phosphate buffer system. In any other buffer systems, i.e. borax, citric acid, ε-aminocaproic acid, and sodium glutamate, the remaining rate was at least 90%. Thus, the latter, and the phosphate buffer system, were shown to have sufficient stability for use. No change in appearance was observed in any of the samples.

3. Effect Of Non-Ionic Surfactant

Polysorbate 80 was applied as a non-ionic surfactant, and the samples were prepared with and without it to compare their stability. However it was found that any emulsified state could not be attained in the sample without polysorbate 80. In addition, it was also found that the degradation of vitamin A in the aqueous preparation became rapid when a non-ionic surfactant with a high peroxide value was used.

4. Effect Of Chelating Agent

Sodium edetate was applied as a chelating agent, and aqueous preparations containing it at concentrations of 0.005%, 0.01%, 0.05% and 0.1% were prepaared. These were stored for 6 weeks at 40° C. and 30° C. with an aqueous preparation containing no sodium edetate. The following results were obtained.

Any of above samples exhibited a sufficient stability, i.e. the remaining rate of vitamin A was not less than 93% at 40° C. and not less than 97% at 30° C. In the sample without sodium edetate, the rate was 90% at 40° C. and 96% at 30° C. The result thus indicated that it is preferable to add sodium edetate in an amount of not less than 0.005% in order to obtain a stable aqueous preparation.

5. Study On Container Materials

Each cut piece of containers for eye drops made of polyethylene, polyethylene terephthalate or polypropylene was put in each glass ampoule, and the aqueous preparation of the present invention was added to it. After stored for 4 days at 60° C. or for 14 days at 50° C., the remaining rate of vitamin A was determined. The results were as follows.

While the remaining rate of vitamin A was lowered to 77% after the 4-day storage at 60° C. due to the adsorption of vitamin A to the container material in the case of polyethylene container, the remaining rate of not less than 80% was observed in other samples. In the test at 50° C. for 14 days, the remaining rate was lowered nearly to 60% in the case of polyethylene, whereas the remaining rate of not less than 70% was observed in other samples, indicating that the latter can be aqueous preparations which allow practical use.

6. Study on Oxygen Scavenger

The aqueous preparation of the present invention was filled in a polypropylene container, and then put in a bag made of laminated aluminum film together with an oxygen scavenger [from MITSUBISHI GAS KAGAKU; AGELESS (trademark) Z-30] to test the stability. While the remaining rate of vitamin A was lowered to about 80% after 6-month storage at room temperature in the case of the sample without the oxygen scavenger, the remaining rate of not less than 95% was observed in the case where the oxygen scavenger was used. In the sample where an oxygen scavenger was used, 93% of vitamin A was found remained after 1 week even under a severe condition of 50° C.

7. Effect of the Preservative

The test of the preservative effect was carried out according to the method of preservative test in the U.S. Pharmacopeia XXI. The following strains of microorganisms were selected for the test.

| | | |
|---|---|---|
| *Staphylococcus aureus* | IFO | 13276 |
| *Escherichia coli* | IFO | 3972 |
| *Pseudomonas aeruginosa* | IFO | 13275 |
| *Candida albicans* | IFO | 1594 |
| *Aspergillus niger* | IFO | 9455 |

The formula of the aqueous preparation used in this test was as follows.

| | |
|---|---|
| retinol palmitate | 200000 I.U. |
| boric acid | 1.7 g |
| sodium edetate | 0.01 g |
| polysorbate 80 | 0.85 g |
| benzalkonium chloride (10%) solution | 0.05 ml |
| borax | q.s. |
| sterile purified water to | 100 ml |
| | pH 7.0 |

The result of the test showed that none of these microorganisms survived on the 14th day after inoculation. Staphylococcus, Escherichia and Pseudomonas, in particular, were not found surfiving on the 7th day after inoculation. Thus, it was demonstrated that the aqueous preparation of the present invention has a sufficient preservative effect for the use as an eye drop.

EXAMPLES

Example 1

| | | |
|---|---|---|
| retinol palmitate | 50000 | I.U. |
| polysorbate 80 | 0.17 | g |
| borax | 0.01 | g |
| boric acid | 1.7 | g |
| sodium edatate | 0.01 | g |
| benzalkonium chloride (10%) solution | 0.05 | ml |
| sterile purified water to | 100 | ml |
| | pH 5.8 | |

Example 2

| | | |
|---|---|---|
| retinol palmitate | 150000 | I.U. |
| polysorbate 80 | 0.51 | g |
| borax | 0.01 | g |
| boric acid | 1.7 | g |
| sodium edetate | 0.01 | g |
| benzalkonium chloride (10%) solution | 0.05 | ml |
| sterile purified water to | 100 | ml |
| | pH 7.0 | |

Example 3

| | | |
|---|---|---|
| retinol palmitate | 200000 | I.U. |
| polysorbate 80 | 0.85 | g |
| borax | 0.01 | g |
| boric acid | 1.7 | g |
| sodium dihydrogen phosphate | 0.2 | g |
| sodium chloride | 0.9 | g |
| sodium edetate | 0.005 | g |
| benzalkonium chloride (10%) solution | 0.05 | ml |
| hydrochloric acid | q.s. | |
| sterile purified water to | 100 | ml |
| | pH 7.0 | |

Example 4

| | | |
|---|---|---|
| retinol palmitate | 200000 | I.U. |
| polyoxyethylenehydrogenated castor oil 60 | 0.5 | g |
| glycerol | 2.6 | g |
| citric acid | 0.2 | g |
| chlorhexidine gluconate (20%) | 0.025 | ml |
| sodium edetate | 0.005 | g |
| sodium hydroxide | q.s. | |
| sterile purified water to | 100 | ml |
| | pH 7.0 | |

Example 5

| | | |
|---|---|---|
| retinol palmitate | 100000 | I.U. |
| polyoxyethylenehydrogenated castor oil 60 | 0.2 | g |
| glycerol | 0.5 | g |
| borax | 0.2 | g |
| boric acid | 1.5 | g |
| benzalkonium chloride (10%) solution | 0.05 | ml |
| sodium edetate | 0.01 | g |
| sterile purified water to | 100 | ml |
| | pH 7.0 | |

Example 6

| | | |
|---|---|---|
| retinol palmitate | 50000 | I.U. |
| polyoxyethylenehydrogenated castor oil 60 | 0.1 | g |
| glycerol | 0.5 | g |
| borax | 0.2 | g |
| boric acid | 1.5 | g |
| benzalkonium cloride (10%) solution | 0.05 | ml |
| sodium edetate | 0.01 | g |
| sterile purified water to | 100 | ml |
| | pH 7.0 | |

What is claimed is:

1. A storage stable sealed pharmaceutical article of manufacture comprising a sealed first container, substantially impervious to atmospheric oxygen, containing an oxygen scavenger and a second container, formed of polypropylene or polyethylene terephthalate, containing an ophthalmic aqueous mixture adapted for the topical treatment of dry eye syndrome of 500 to 3,000 I.U./ml of retinol palmitate; as a buffering agent, boric acid and/or borax in the range of 1.0 to 2.0%; as a non-ionic surfactant, polysorbate 80 or polyoxyethylene-hydrogenated castor oil in the range of 1.5 to 5 parts by weight per 1 part by weight of the retiol palmitate; as a chelating agent, sodium edetate in the range of 0.001 to 0.1%; as a preservative, benzalkonium chloride; as an isotonizer, glycerol; and having a pH in the range of 5 to 8.

2. An article of manufacture according to claim 1 wherein the second container contains a plurality of doses of the ophthalmic mixture.

* * * * *